(12) United States Patent
Yang et al.

(10) Patent No.: US 8,119,610 B2
(45) Date of Patent: Feb. 21, 2012

(54) METHOD FOR EFFICIENT RNA INTERFERENCE IN MAMMALIAN CELLS

(75) Inventors: Dun Yang, San Francisco, CA (US); J. Michael Bishop, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 750 days.

(21) Appl. No.: 10/448,612

(22) Filed: May 29, 2003

(65) Prior Publication Data

US 2004/0014113 A1 Jan. 22, 2004

Related U.S. Application Data

(60) Provisional application No. 60/385,011, filed on May 31, 2002.

(51) Int. Cl.
*A61K 31/70* (2006.01)
*C07H 21/04* (2006.01)
*C12Q 1/68* (2006.01)
(52) U.S. Cl. .............................. 514/44; 536/24.5; 435/6
(58) Field of Classification Search ................. 536/23.1; 436/6; 514/44
See application file for complete search history.

(56) References Cited

U.S. PATENT DOCUMENTS

| 6,329,203 B1 * | 12/2001 | Bennett et al. ................. 435/377 |
| 6,737,512 B2 | 5/2004 | Wu et al. |
| 2002/0162126 A1 * | 10/2002 | Beach et al. ...................... 800/8 |
| 2003/0100127 A1 * | 5/2003 | Corn et al. ..................... 436/518 |
| 2003/0114410 A1 | 6/2003 | Neufeld et al. |
| 2004/0033602 A1 | 2/2004 | Ford et al. |
| 2004/0038278 A1 | 2/2004 | Tzertzinis et al. |
| 2007/0155684 A1 | 7/2007 | Maina et al. |

OTHER PUBLICATIONS

Agrawal et al. Molecular Medicine Today, 2000, vol. 6, p. 72-81.*
Opalinska et al. Nature Reviews Drug Discovery, 2002, vol. 1, p. 503-514.*
Check Nature, 2003, vol. 425, p. 10-12.*
Elbashir et al. Genes and Development 2001, vol. 15, pp. 188-200.*
Elbashir et al. Nature 2001, vol. 411, pp. 494-498.*
Amarasinghe et al. Methods in Enzymology 2001 vol. 342, pp. 143-158.*
Amarasinghe, Asoka K. et al.; "*Escherichia coli* Ribonuclease III: Affinity Purification of Hexahistidine-Tagged Enzyme and Assays for Substrate Binding and Cleavage"; *Methods in Enzymology*; 2001; pp. 143-158; vol. 342.
Bernstein, Emily et al.; "Role for a Bidentate Ribonuclease in the Initiation Step of RNA Interference"; Letters to *Nature*; Jan. 18, 2001; pp. 363-366; vol. 409.
Brummelkamp, Thijn R. et al.; "A System for Stable Expression of Short Interfering RNAs in Mammalian Cells"; *Science*; Apr. 19, 2002; pp. 550-553; vol. 296.

Caplen, Natasha J. et al.; "Specific Inhibition of Gene Expression by Small Double-Stranded RNAs in Invertebrate and Vertebrate Systems"; *PNAS*; Aug. 14, 2001; pp. 9742-9747; vol. 98, No. 17.
Elbashir, Sayda M. et al.; "Duplexes of 21-Nucleotide RNAs Mediate RNA Interference in Cultured Mammalian Cells;" Letters to *Nature*; May 24, 2001; pp. 494-498; vol. 411.
Elbashir, Sayda M. et al.; "Functional Anatomy of siRNAs for Mediating Efficient RNAi in *Drosophila melanogasfer* Embryo Lysate"; *The EMBO Journal*; 2001; pp. 6877-6888; vol. 20, No. 23.
Paddison, Patrick J. et al.; "Short Hairpin RNAs (shRNAs) Induce Sequence-Specific Silencing in Mammalian Cells"; *Genes & Development*; 2002; pp. 948-958; vol. 16.
Paddison, Patrick J. et al.; "Stable Suppression of Gene Expression by RNAi in Mammalian Cells" *PNAS*; Feb. 5, 2002; pp. 1443-1448; vol. 99, No. 3.
Yang, Dun et al.; "Evidence that Processed Small dsRNAs May Mediate Sequence-Specific mRNA Degradation During RNAi in *Drosophila* Embryos"; *Current Biology*; 2000; pp. 1191-1200; vol. 10.
Holen, T. et al., "Positional Effects of Short Interfering RNAs Targeting the Human Coagulation Trigger Tissue Factor," *Nucleic Acids Res*. 30(8):1757-66 (2002).
Agrawal, N. et al. "RNA Interference: Biology, Mechanism, and Applications," Dec. 2003, *Microbiology and Molecular Biology Reviews*, vol. 67, No. 4, pp. 657-685.
Blaszczyk, J. et al. "Crystallographic and Modeling Studies of RNase III Suggest a Mechanism for Double-Stranded RNA Cleavage," Dec. 2001, *Structure*, vol. 9, pp. 1225-1236.
Sijen, T. et al. "On the Role of RNA Amplification in dsRNA-Triggered Gene Silencing," Nov. 16, 2001, *Cell*, vol. 107, pp. 465-476.
Suppliementary European Search Report mailed on Aug. 24, 2007, for EP Application No. 03756319.4, five pages.
Timmons, L. et al. "Ingestion of Bacterially Expressed dsRNAs Can Produce Specific and Potent Genetic Interference in *Caenorhabditis elegans*," 2001, *Gene*, vol. 263, pp. 103-112.
Zamore, P.D. "Thirty-Three Years Later, a Glimpse at the Ribonuclease III Active Site," Dec. 2001, *Molecular Cell*, vol. 8, pp. 1158-1160.
Zhang, H. et al. "Single Processing Center Models for Human Dicer and Bacterial RNase III," Jul. 9, 2004, *Cell*, vol. 118, pp. 57-68.
Conrad, Christian et al., "Ribonuclease III: new sense from nuisance," *J. Biochem & Cell Biol*. 34:116-129 (2002).
Court, Donald, "RNA Processing and Degradatin by RNase III," In *Control of Messenger RNA Stability*, J.G. Belasco and G. Braverman, eds. (New York, NY: Academic Press), 71-116 (1993).
Yang, Dun et al. "Short RNA duplexes produced byhydrolysis with *Escherivia coli* RNase III mediate effective RNA interference in mammalian cells," *PNAS* 99(15): 9942-9947 (Jul. 23, 2002). Zamore, Phillip D. et al., "RNAi: Double-Stranded RNA Directs the ATP-Dependent Cleavage of mRNA at 21 to 23 Nucleotide Intervals," *Cell*, 101:25-33 (Mar. 31, 2000).
Zhang, Kejing et al., "Regulation of ribonuclease III processing by double-helical sequence antideterminants," *Proc. Natl. Acad. Sci. USA*, 94:13437-13441 (Dec. 1997).
Applied Biosystems Ambion®, "RNase III, *E. coli*," Catalog No. AM2290, Data Sheet, Oct. 25, 2007, 2 pages.
Edy, V.G. et al., "Action of Nucleases on Double-Stranded RNA," *Eur. J. Biochem*., 1976, vol. 61, pp. 563-572.

(Continued)

*Primary Examiner* — Tracy Vivlemore

(74) *Attorney, Agent, or Firm* — Kilpatrick Townsend & Stockton LLP

(57) ABSTRACT

The present invention relates to methods of making RNAi libraries using *E. coli* RNAse III for inhibition of mammalian gene expression.

11 Claims, 7 Drawing Sheets

OTHER PUBLICATIONS

Jackson, A.L. et al., "Expression Profiling Reveals Off-Target Gene Regulation by RNAi," *Nature Biotechnology*, Jun. 2003, vol. 21, No. 6, pp. 635-637, Erratum/Corrigendum, 2003, 1 page.

Jackson, A.L. et al., "Noise Amidst the Silence: Off-Target Effects of siRNAs?" *TRENDS in Genetics*, Nov. 2004, vol. 20, No. 11, pp. 521-524.

Kittler, R. et al., "Production of Endoribonuclease-prepared Short Interfering RNAs for Gene Silencing in Mammalian Cells," *Nature Methods*, Oct. 2005, vol. 2, No. 10, pp. 779-784.

Kittler, R. et al., "Genome-Wide Resources of Endoribonuclease-prepared Short Interfering RNAs for specific Loss-of-Function Studies," *Nature Methods*, Apr. 2007, vol. 4, No. 4, pp. 337-344.

New England Biolabs® Inc., "ShortCut® RNase III," located at <http://www.neb.com/nebecomm/products/productM0245.asp>, last visited on Jul. 31, 2008, 3 pages.

Yang, D. et al., "RNA Interference (RNAi) With RNase III-Prepared siRNAs," *Methods in Molecular Biology*, 2004, vol. 252, pp. 471-482.

Agami, Reuven, "RNAi and related mechanisms and their potential use for therapy," *Current Opinion in Chemical Biology* (2002) 6:829-834.

* cited by examiner

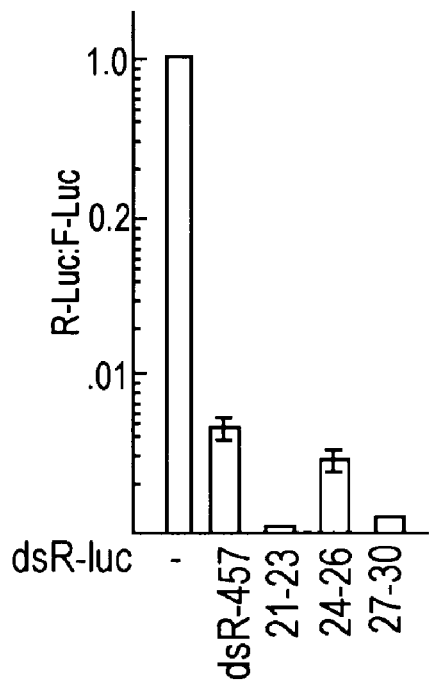 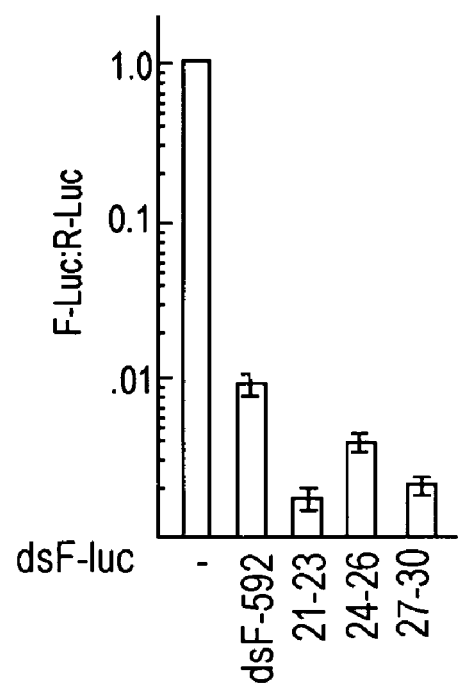
FIG. 2A  FIG. 2B
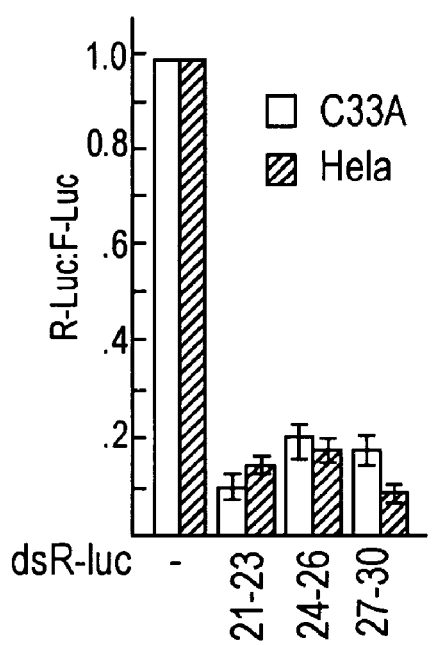 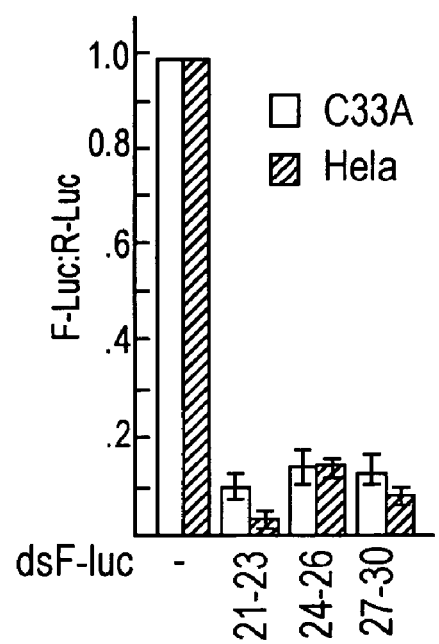
FIG. 2C  FIG. 2D

METHOD FOR EFFICIENT RNA INTERFERENCE IN MAMMALIAN CELLS

CROSS-REFERENCES TO RELATED APPLICATIONS

The present application claims benefit of priority to U.S. Provisional Patent Application No. 60/385,011, filed May 31, 2002, which is incorporated by reference in its entirety.

STATEMENT AS TO RIGHTS TO INVENTIONS MADE UNDER FEDERALLY SPONSORED RESEARCH AND DEVELOPMENT

This invention was made with government support under NIH grant CA44338. The Government has certain rights in this invention.

BACKGROUND OF THE INVENTION

Posttranscriptional gene silencing or RNA interference (RNAi) has been reported to be accompanied by the accumulation of small (20-25, e.g., 20, 21, 22 nucleotide) fragments of double stranded RNA, which are reported to be synthesized from an RNA template (Hamilton & Baulcombe, *Science* 286:950-952 (1999)). These fragments are called small interfering RNAs (siRNAs). It has become clear that in a range of organisms, including mammals, siRNA is an important component leading to gene silencing (Fire et al., *Nature* 391:806-811 (1998); Timmons & Fire, *Nature* 395:854 (1998); WO99/32619; Kennerdell & Carthew, *Cell* 95:1017-1026 (1998); Ngo et al., *Proc. Nat'l Acad. Sci. USA* 95:14687-14692 (1998); Waterhouse et al., *Proc. Nat'l Acad. Sci. USA* 95:13959-13964 (1998); WO99/53050; Cogoni & Macino, *Nature* 399:166-169 (1999); Lohmann et al., *Dev. Biol.* 214:211-214 (1999); Sanchez-Alvarado & Newmark, *Proc. Nat'l Acad. Sci. USA* 96:5049-5054 (1999); Elbashir et al., *Nature* 411:494-297 (2001)). As gene silencing is a powerful tool for regulation of gene expression, both of endogenous genes and of transgenes, improved methods of gene silencing and improved methods of making siRNA libraries are desired.

SUMMARY OF THE INVENTION

Small interfering RNA (siRNA) has became a powerful tool to selectively silence gene expression in cultured mammalian cells. Because different siRNAs of the same gene have variable silencing capacities, RNA interference with synthetic siRNA can be inefficient and cost intensive, especially for functional genomic studies. In the present invention, *E. coli* RNase III is used to cleave double-stranded RNA into esiRNA (endoribonuclease-prepared siRNA) that can target multiple sites within an mRNA. The invention therefore provides an RNA duplex pool that can recognize multiple sites in any particular RNA to silence gene expression. In contrast to long double-stranded RNA, esiRNA mediates effective RNA interference without apparent non-specific effect in cultured mammalian cells. Sequence-specific interference by esiRNA and the non-specific interferon response activated by long dsRNA are independent pathways in mammalian cells. EsiRNA works by eliciting the destruction of its cognate mRNA. Because of its simplicity and potency, this approach is useful for analysis of mammalian gene functions. In addition, this approach is useful for functional genomic screens to identify genes associated with a selected phenotype, such as a disease phenotype, in order to identify genes that can be used as targets for drug discovery and diagnostic applications.

BRIEF DESCRIPTION OF THE DRAWINGS

FIGS. 2A-F: siRNA-mediated gene silencing in insect and mammalian cells. The effect of esiRNA on R-luc (a, c) or F-luc (b, d) expression was determined in *Drosophila* S2 cells (a, b) and mammalian cell lines, Hela and C33A (c, d). Plasmid DNAs with or without various sized dsRNAs were cotransfected into cells. (e) Reporter plasmids, siRNAs, dsR-NAs and short hairpin RNAs. For Firefly (F-luc) and *Renilla reniformis* (R-luc) luciferase genes, the diagram illustrates DNA constructs used to produce in vivo mRNA and in vitro dsRNA. The positions of dsRNAs, chemically synthesized siRNAs (CS1 and CS2), in vitro transcribed siRNAs (T1 to T6) and short hairpin RNAs (H1 to H6) are indicated. (f) The variable effect of synthetic siRNAs or short hairpin RNAs on different sequences within a gene. Plasmid DNAs with or without the various indicated short RNA species were cotransfected into Hela cells. R is the F-luc esiRNA shorter than 30 bp.

DETAILED DESCRIPTION OF THE INVENTION

Introduction

Figures 1A, 1B, 1C:
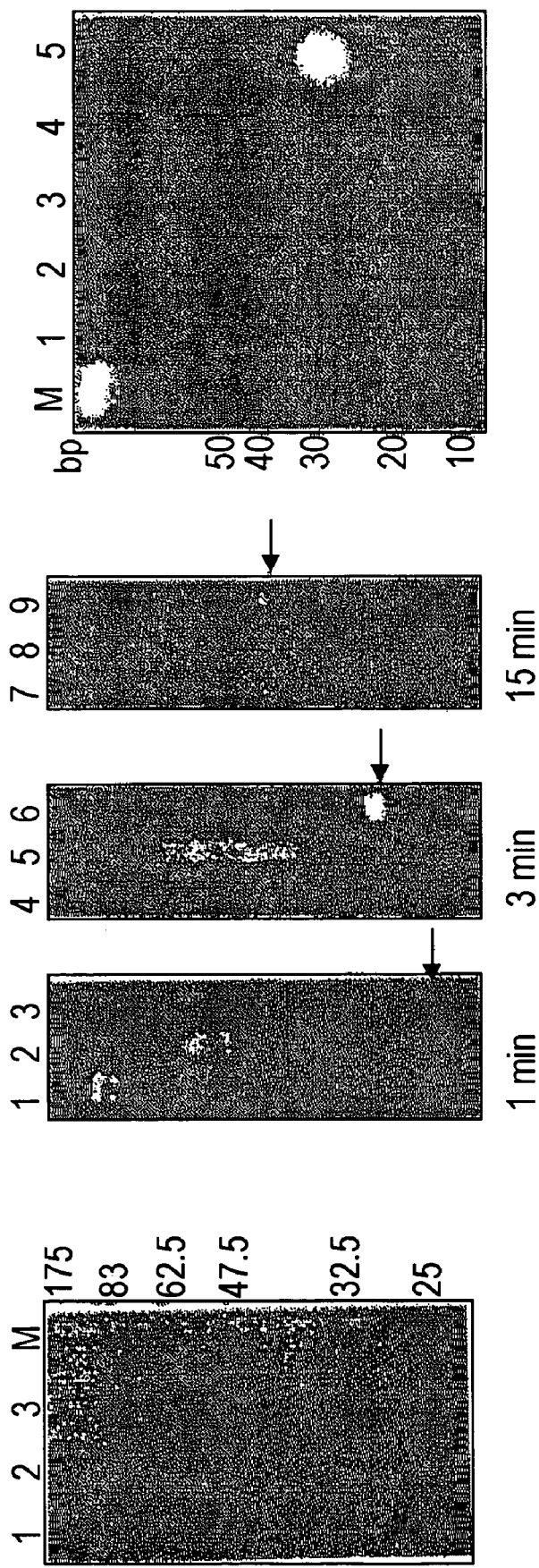
FIGS. 1A-C: Preparation of siRNA from dsRNA by hydrolysis with *E. coli* RNase III. (a) Overexpression and purification of GST-RNase III fusion. Lane 1 and 2, *E. coli* extracts before and after IPTG induction; Lanes 3, purified GST-RNase III fusion; Lane M, protein molecular weight marker. (b) Time course of RNase III digestion of dsRNA. DsR-457 or dsF-592 RNA was incubated with RNase III for indicated time, and then separated by electrophoresis in a 4% agarose gel. Lanes 1, 4 and 7 are dsR-457; Lanes 2, 5 and 8 are dsF-592; Lanes 3, 6 and 9 are 21 bp siRNA marked by an arrow. (c) Agarose gel analysis of purified short RNA species processed from dsF-592. Lane M, 10 bp DNA marker; Lane 1 and 2 are chemically synthesized siRNAs. Lane 3, 21-23 bp; lane 4, 24-26 bp; Lane 5, 27-30 bp.

Double-stranded RNA interference, or RNAi, has became a powerful genetic tool to selectively silence gene expression in many eukaryotes (1-2). In the RNAi reaction, the cellular RNase III enzyme Dicer cleaves the dsRNA silencing trigger into 21-25 nucleotide RNA called siRNA (small interfering RNA) (3-4). SiRNA pairs with its cognate mRNA, leading to degradation of target mRNA and amplification of gene-specific silencing signals (1-5). Although RNAi has also been observed in mouse oocytes, embryos, embryonic stem cells and embryonal carcinoma cell lines, double-strand RNA (dsRNA) triggers non-specific inhibition of gene expression in most mammalian cell lines (6-8). In mammalian cells, dsRNAs longer than 30 base pairs can activate the dsRNA-dependent kinase PKR and 2'-5'-oligoadenylate synthetase, normally induced by interferon (9). By virtue of its small size, synthetic siRNA avoids activation of the interferon response. The activated PKR inhibits general translation by phosphorylation of the translation factor eukaryotic initiation factor 2α (eIF2α), while 2'-5'-oligoadenylate synthetase causes nonspecific mRNA degradation via activation of RNase L (9).

In contrast to the nonspecific effect of long dsRNA, siRNA can mediate selective gene silencing in the mammalian system (10-11). Hairpin RNA with a short loop and 19 to 27 base pairs in the stem also selectively silences expression of genes that are homologous to the sequence in the double-stranded stem (12-13). Mammalian cells can convert short hairpin RNA into siRNA to mediate selective gene silencing (12-13). Although many mammalian cells can also convert long dsRNA into siRNA, long dsRNA is incapable of triggering RNAi in these cells (7). The inability of long dsRNA to elicit RNAi in the vertebrate system has been generally attributed to non-specific activation of the interferon response (7-8). However, the relationship between the interferon signaling pathway and RNA interference has not been definitely addressed.

Although siRNA provides a promising tool to assess the consequences of suppressing gene expression in cultured mammalian cells, RNAi with synthetic siRNA is limited because siRNAs to different sequences within a gene have dramatically varied inhibitory ability (14-15). Therefore, each mRNA must be screened for an efficient siRNA, a laborious and costly process. However, processing of long dsRNAs should generate a great variety of siRNAs capable of interacting with multiple sites on target mRNAs, increasing the chance that at least one siRNA will pair with its target sequence. Thus, the power of siRNA as a genetic tool in the mammalian system could be greatly enhanced by using siRNA processed from dsRNA.

Although Dicer is involved in the dsRNA cleavage in vivo, using Dicer to prepare siRNA in vitro may be problematic because dsRNA cleavage by Dicer is very inefficient, particularly for short dsRNAs (3, 16). In contrast, E. coli RNase III (RNase III, EC3.1.24) can digest dsRNA very efficiently into short pieces with the same end structures as siRNA, 5' phosphate/3' hydroxyl termini and 2- to 3-nucleotide 3' overhangs (17). These end structures of siRNA are reported to be important for RNAi activity (18). In addition, large amounts of soluble recombinant E. coli RNase III protein can be obtained (17). These attributes make E. coli RNase III a promising enzyme to prepare siRNAs and siRNA libraries in vitro.

Exhaustive cleavage of dsRNA by E. coli RNase III leads to duplex products averaging 12-15 bp in length (17). These short dsRNA are unable to trigger an RNAi response in mammalian cells (6). To obtain siRNA of appropriate length, performed limited RNase III digestion of dsRNA was performed, efficiently generating 20-25 bp siRNA. These siRNAs recapitulated the potent and sequence-specific gene silencing by long dsRNA in Drosphila S2 cells. More importantly, they also mediated effective RNAi without non-specific effects in mammalian cells. SiRNA produced by the method successfully inhibited various endogenous genes in different mammalian cell lines. Because it is relatively quick and simple, this method is useful in utilizing siRNA for analysis of gene functions in cultured mammalian cells.

Definitions

A "target gene" refers to any gene suitable for regulation of expression, including both endogenous chromosomal genes and transgenes, as well as episomal or extrachromosomal genes, mitochondrial genes, chloroplastic genes, viral genes, bacterial genes, animal genes, plant genes, protozoal genes and fungal genes.

An "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

"Inverted repeat" refers to a nucleic acid sequence comprising a sense and an antisense element positioned so that they are able to form a double stranded siRNA when the repeat is transcribed. The inverted repeat may optionally include a linker or a heterologous sequence such as a self-cleaving ribozyme between the two elements of the repeat. The elements of the inverted repeat have a length sufficient to form a double stranded RNA. Typically, each element of the inverted repeat is about 15 to about 100 nucleotides in length, preferably about 20-30 base nucleotides, preferably about 20-25 nucleotides in length, e.g., 20, 21, 22, 23, 24, 25, 26, 27, 28, 29, or 30 nucleotides in length.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 6-7 amino acids or 25 nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "inhibiting expression of a target gene" refers to the ability of a siRNA of the invention to initiate gene silencing of the target gene. To examine the extent of gene silencing, samples or assays of the organism of interest or cells in culture expressing a particular construct are compared to control samples lacking expression of the construct. Control samples (lacking construct expression) are assigned a relative value of 100%. Inhibition of expression of a target gene is achieved when the test value relative to the control is about 90%, preferably 50%, more preferably 25-0%. Suitable assays include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), digoxigenin, biotin, luciferase, CAT, beta galactosidase, GFP, or haptens and proteins which can be made detectable, e.g., by incorporating a radiolabel into the peptide or used to detect antibodies specifically reactive with the peptide.

"Biological sample" includes tissue; cultured cells, e.g., primary cultures, explants, and transformed cells; cellular extracts, e.g., from cultured cells or tissue, cytoplasmic extracts, nuclear extracts; blood, etc. Biological samples include sections of tissues such as biopsy and autopsy samples, and frozen sections taken for histologic purposes. A biological sample, including cultured cells, is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

esiRNA Synthesis

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

An RNA population can be used to provide long precursor RNAs, or long precursor RNAs that have substantial or complete identity to a selected target sequence can be used to make the esiRNA of the invention. The RNAs can be isolated from cells or tissue, synthesized, and/or cloned according to methods well known to those of skill in the art. The RNA can be a mixed population (obtained from cells or tissue, transcribed from cDNA, subtrated, selected etc.), or can represent a single target sequence. RNA can be naturally occurring, e.g., isolated from tissue or cell samples, or synthesized in vitro, e.g., using T7 or SP6 polymerase and PCR products or a cloned cDNA. Both selected target RNAs and RNA populations can be synthesized in vitro.

To form a long dsRNA, for synthetic RNAs, the complement is also transcribed in vitro and hybridized to form a ds RNA. If a naturally occuring RNA population is used, the RNA complements are also provided (to form dsRNA for digestion by *E. coli* RNAse III), e.g., by transcribing cDNAs corresponding to the RNA population, or by using RNA polymerases. The precursor RNAs are then hybridized to form double stranded RNAs for RNAse II digestion. The ds RNAs are then digested in vitro with *E. coli* RNAse III (either recombinant or naturally occurring) to the methods described herein.

Methods for isolating RNA, synthesizing RNA, hybridizing nucleic acids, making and screening cDNA libraries, and performing pCR are well known in the art (see, e.g., Gubler & Hoffman, *Gene* 25:263-269 (1983); Sambrook et al., supra; Ausubel et al., supra), as are PCR methods (see U.S. Pat. Nos. 4,683,195 and 4,683,202; *PCR Protocols: A Guide to Methods and Applications* (Innis et al., eds, 1990)). Expression libraries are also well known to those of skill in the art.

Transformation of Prokaryotes and Eukaryotes

Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983). Any of the well-known procedures for introducing foreign nucleotide sequences into host cells may be used. These include the use of naked nucleic acids, viral transduction, calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA, RNA (either naturally occurring or synthetic) or other foreign genetic material into a host cell (see, e.g., Sambrook et al., supra). It is only necessary that the particular genetic engineering procedure used be capable of successfully introducing an esiRNA into the host cell.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

I. Results and Discussion

A. Processing long dsRNAs into short RNA duplexes using *E. coli* RNase III

Figure 2E:
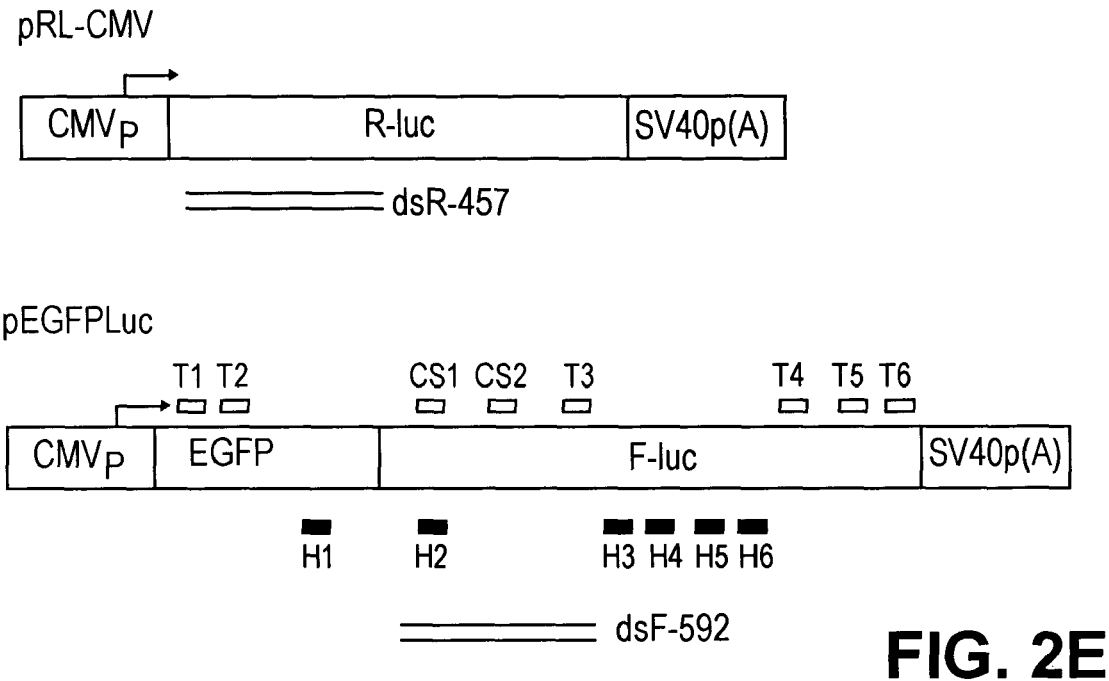

To prepare a heterogeneous siRNA population that could potentially target multiple sites per mRNA molecule for inhibition, we used *E. coli* RNase III to digest long dsRNAs representing the mRNA targets. We overexpressed *E. coli* RNase III as a GST fusion protein in *E. coli* and purified it to homogeneity (FIG. 1a). To make a 592 bp dsRNA (dsF-592) corresponding to the firefly luciferase (F-luc) and a 457 bp dsRNA (dsR-457) of *Renilla* luciferase (R-luc), we performed in vitro transcription from PCR products that had appended phage promoters at each ends (FIG. 2e). We found that GST-RNase III fusions were highly active in cleaving these dsRNAs at 37° C. Even at low RNase III concentrations, cleavage products were visible within 1 min incubation, and molecules approximately 15-30 bp in length were accumulated during longer incubation and became the main products (FIG. 1b). Similar digestion patterns were also observed with dsRNAs representing more than 20 other genes (data not shown). After optimization, we found that limited RNase III digestion of dsRNA at room temperature for one hour yielded ample amounts of esiRNA for inhibition of most genes. Efficiently processing dsRNA with high sequence complexity into short species is consistent with the lack of sequence-specificity in substrate recognition and cleavage by *E. coli* RNase III (19). We separated RNase III-digestion products on polyacrylamid gels and purified the RNAs corresponding to approximately 21-23, 24-26, and 27-30 bp (FIG. 1c). For simplicity, we named siRNA prepared by RNase III digestion as esiRNA (endoribonuclease-prepared siRNA).

B. EsiRNA Mediates Effective RNAi Against Reporter Gene Expression in Cultured Insect and Mammalian Cells To test if esiRNA has RNAi activity, we cotransfected short RNA duplexes along with expression constructs for F-luc and R-luc into *Drosophila* S2 cells. Inhibition was estimated by measuring the relative F-luc (F-luc/R-luc) or relative R-luc (R-luc/F-luc) activity as described previously (16). We observed that the 21-23 bp esiRNA, processed from dsR-457, caused about 900-fold inhibition of R-luc activity (FIG. 2a). The similarly sized esiRNA of F-luc exerted 500-fold of inhibition of F-luc activity (FIG. 2b). 24-26 bp and 27-30 bp esiRNAs showed similarly potent inhibition of their cognate luciferase activity (FIG. 2a, b). The unprocessed dsRNAs, dsR-457 and dsF-592, were 2-10 fold less potent than esiRNA(FIG. 2a, b). Recapitulation of RNAi activity of long dsRNA with its esiRNA is consistent with the presumption that siRNA is the bone fide mediator of the RNAi reaction.

Figure 2F:
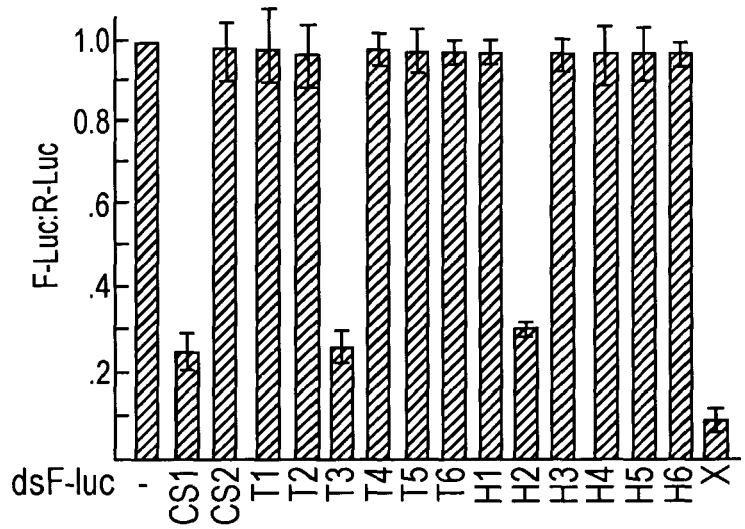

We further tested if esiRNA is a specific gene silencer in mammalian cells. We observed that 21-23 bp esiRNA of R-luc caused 85-90% inhibition of relative R-luc expression in both Hela and C33A cells (FIG. 2c). Similarly sized esiRNAs of F-luc inhibited 90-95% of relative F-luc expression (FIG. 2d). This reciprocal effect indicates that the short RNA duplexes acted in a sequence-specific manner without affecting expression from the non-complementary templates. Similarly, 24-26 bp and 27-30 bp esiRNAs exerted sequence-specific inhibition, consistent with a published report that the synthetic EGFP siRNAs ranging from 21 to 27 nucleotides all have RNAi activity (FIG. 2c, d and Ref. 11). Similar results were obtained with column-purified esiRNAs (FIG. 2f). We compared inhibitory ability of siRNA and esiRNA. We found that different siRNAs of F-luc made by either chemical synthesis or in vitro transcription had dramatically varied silencing ability and were less potent inhibitors than esiRNA (FIG. 2d, f). This was also true for short RNA hairpins. Of the 14 siRNAs and short hairpin RNAs for F-luc, only three showed reasonable RNAi activity (FIG. 2f). The synthetic siRNAs or hairpin RNAs recognized only one sequence element, whereas esiRNAs covered comprehensive sequence elements of the target mRNA. Thus, esiRNA likely increases the chance that at least one siRNA can pair with and lead to destruction of its target.

Similar strong and specific inhibition by esiRNA was observed in IMR-90, CHO, hTERT-RPE1, MEF and 293 cells, suggesting the approach is generally applicable for mammalian cell lines. As expected, long dsRNA, either dsF-592 or dsR-457, caused sequence-independent inhibition of both F-luc and R-luc expression, suggesting activation of the interferon signaling pathway (FIG. 3e, f). In contrast, esiRNA did not cause significant non-specific inhibition of control luciferase expression in these mammalian cell lines.

C. Characteristics of RNAi Mediated by esiRNA in Mammalian Cells: Dose-Dependence Cotransfection assays do not allow accurate calculation of the minimal effective esiRNA concentration. To study dose-dependence of esiRNA-induced inhibition, we used F-luc esiRNA to inhibit gene expression in the hTERT-RPE1 cells that were stably transfected with an F-luc expression construct. We observed a saturated inhibition when the transfection buffer contained at least 3 nM of esiRNA (FIG. 3a). Inhibition decreased at sub-saturating esiRNA doses and was undetectable when the esiRNA dose was below 0.5 nM (FIG. 3a). The antisense strand of the chemically synthesized siRNA CS1 was incapable of inhibiting F-luc activity even at 10- to 20-fold higher concentrations than the effective concentration used for its double-stranded form, suggesting siRNAs are more potent inhibitors than antisense RNAs (FIGS. 2f, 3a).

D. Rapid Onset and Prolonged Duration of Inhibition

To further characterize the RNAi reaction, we determined the duration of F-luc esiRNA-mediated inhibition of chromatin templates in the above hTERT-RPE1 cells. We observed 50% to 65% inhibition of F-luc activity at 8 hours after transfection, suggesting that silencing was established rapidly. Silencing reached the maximum 5 to 6 days after transfection and then declined (FIG. 3b). When plasmid DNA was used to express targets for inhibition in Hela cells, we observed that the inhibition could last 2 weeks if high esiRNA doses were used. Low doses of esiRNA caused less potent inhibition that was sustained for several days (FIG. 3b). Thus, the longevity of esiRNA-mediated inhibition was at least partially dependent on esiRNA dose with either episomal or chromatin templates. The rapidity and longevity of esiRNA-mediated inhibition suggests that esiRNAs could be used to inactivate genes whose protein products are relatively stable.

E. EsiRNA Elicits mRNA Decay

A key feature of RNAi in *C. elegance* and *Drosophila* is that it exerts its effect by eliciting the destruction of targeted mRNA (1). To test if siRNAs also act post-transcriptionally in the mammalian system, we asked if esiRNA could directly inhibit expression from its cognate mRNA. We cotransfected esiRNA and F-luc mRNA into Hela cells. Three hours following transfection, control cells that had received F-luc mRNA produced 20000-50000 units of luciferase activity.

Figure 3C:
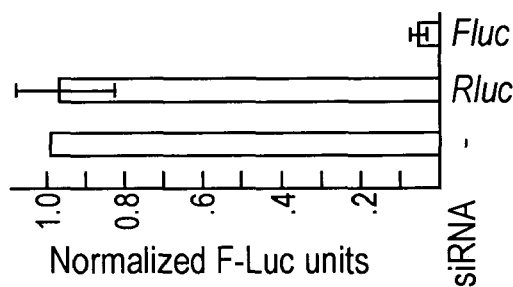
FIGS. 3A-F: Characteristics of RNAi. (a) Dose-response for antisense RNA (asRNA) and esiRNA against F-luc. Indicated amounts of F-luc esiRNA (21-23 bp) or antisense strand of CS1 were transfected into RPE cells to target F-luc expression from chromatin templates, and luciferase activities were measured at 24 hours after transfection. Data represented the average of 3-6 experiments and were expressed as relative luciferase activity after normalization to the luciferase units/ ug of protein observed in control cells transfected with R-luc siRNA. (b) Duration of esiRNA-mediated inhibition. F-luc esiRNA (21-23 bp) was transfected into RPE cells and luciferase activities were measured at the indicated time period. When Hela cells were used, F-luc target was expressed from cotransfected plasmid DNA. (c) EsiRNA silences gene expression from mRNA templates. Hela cells were transfected with 0.5 µg F-luc mRNA with or without 0.1 µg of esiRNA (21-23 bp) for either F-luc or R-luc for 3 hours and then collected for luciferase assays. Data were expressed as arbitrary luciferase units and normalized to that produced in cells transfected with mRNA-only. (d) EsiRNA corresponding to the promoter region has no RNAi activity. Hela cells were transfected with pGL-3-control (Promega) and pRL-CMV with or without 21-23 bp esiRNA corresponding to either the CMV promoter or R-luc. Luciferase activity was measured 24 to 96 hours after cotransfection. (e, f) Relationship between RNAi and the interferon signaling pathway. DsF-592 and F-luc esiRNA (21-23 bp) were transfected individually or together into Hela cells to silence F-luc expression from plasmid templates. Luciferase activity was measured 24 to 48 hours after cotransfection. Data were expressed as either F-luc units (e) or relative F-luc activity (f) and then normalized to that of DNA-only transfections.
Figure 3D:
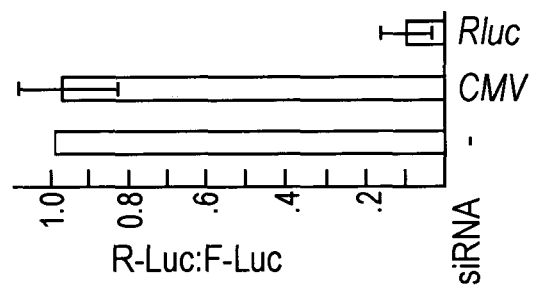
Figure 3A:
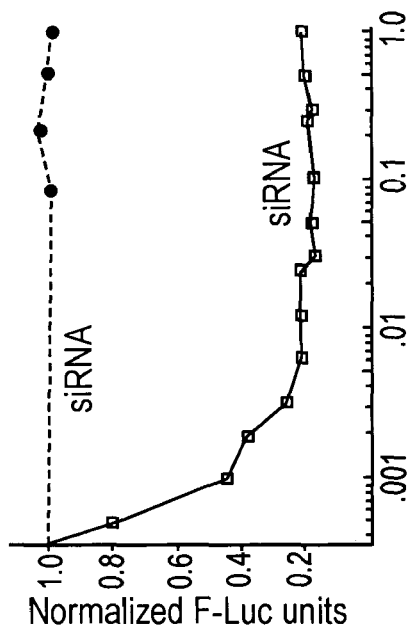
Figure 3B:
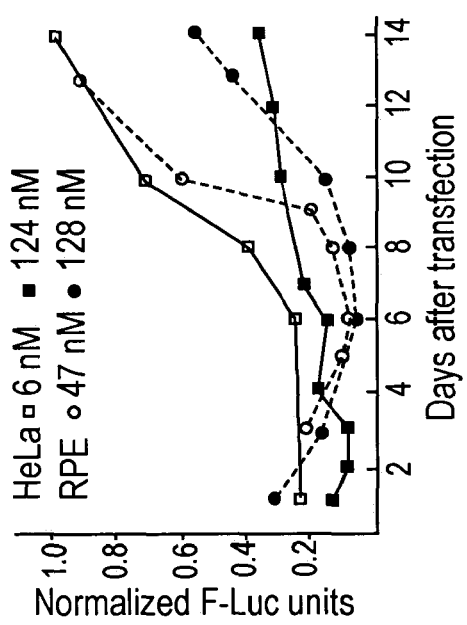
Figure 3E:
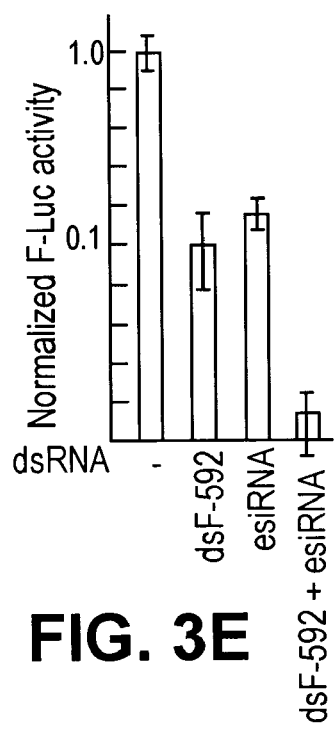
Figure 4:
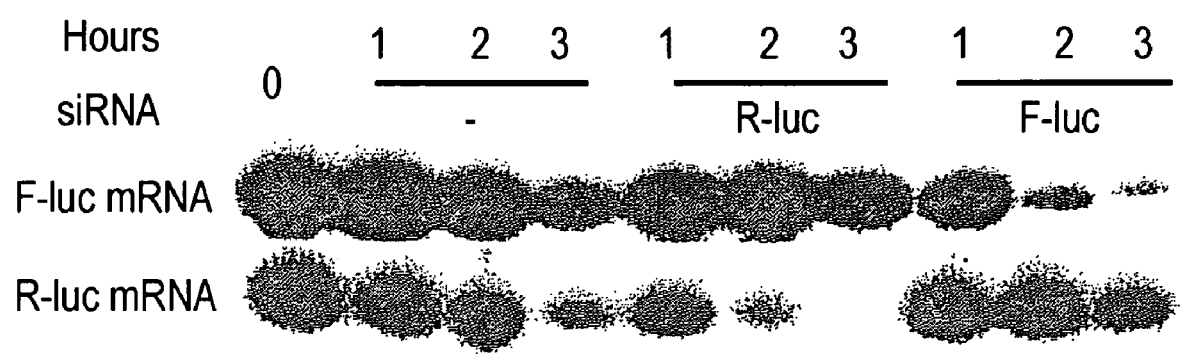
FIG. 4: EsiRNA induces degradation of its cognate mRNA. $^{32}$P-labelled F-luc or R-luc mRNA was incubated in extracts of Hela cells with or without its cognate esiRNAs for indicated time period and then analyzed in a 4% sequence gel.

However, cotransfected esiRNAs for F-luc but not R-luc caused 15-fold inhibition of F-luc activity, suggesting that siRNA-mediated gene silencing is directed at mRNA in mammalian cells (FIG. 3c). Consistent with this, we found that the esiRNA corresponding to a promoter region had no RNAi activity (FIG. 3d). To test if esiRNA elicits destruction of the target mRNA, we used an extract of Hela cells to perform an in vitro RNAi assay identical to that used to characterize RNAi responses in Drosophila embryo extracts (20). We found that esiRNAs for either F-luc or R-luc accelerated the degradation of their cognate mRNA 4- to 8-fold (FIG. 4). This is consistent with previous reports on the effect of siRNA (10, 14).

Figure 3F:
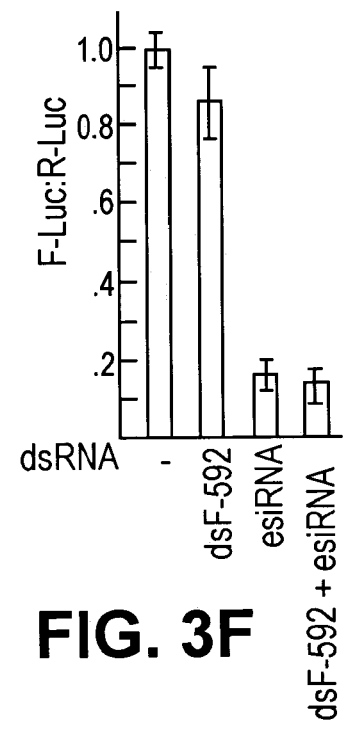

F. Non-Specific Gene Silencing by Long dsRNA and Sequence-specific Interference by siRNA are Independent Pathways To test the effect of the interferon signaling pathway on RNAi, we first asked if we could detect RNAi activity of siRNA in the presence of a non-specific interferon response activated by long dsRNA in Hela cells. We found that dsF-592 caused 10- to 20-fold inhibition of both F-luc and R-luc expression, suggesting activation of the non-specific interferon response (FIG. 3e, f). F-luc esiRNA selectively inhibited F-luc expression as observed before. When esiRNA and dsF-592 were cotransfected, we observed additive inhibition of F-luc expression (FIG. 3e). However, esiRNA inhibited relative F-luc activity equally with or without cotransfected dsF-592, suggesting that activation of non-specific interferon response has no effect on the potency of specific RNAi inhibition (FIG. 3f).

We then tested if inactivation of the interferon response suffices to activate specific gene silencing of long dsRNA. We found that mouse embryonic fibroblast cells lacking either PKR or both PKR and RNase L were defective in both non-specific and specific gene silencing triggered by dsF-592, although siRNA-mediated RNAi could be detected (data not shown). We concluded that sequence-specific RNA interference mediated by siRNA is independent of dsRNA-triggered non-specific gene silencing.

G. EsiRNA Selectively Silences the Expression of Endogenous Genes

Figure 5A:
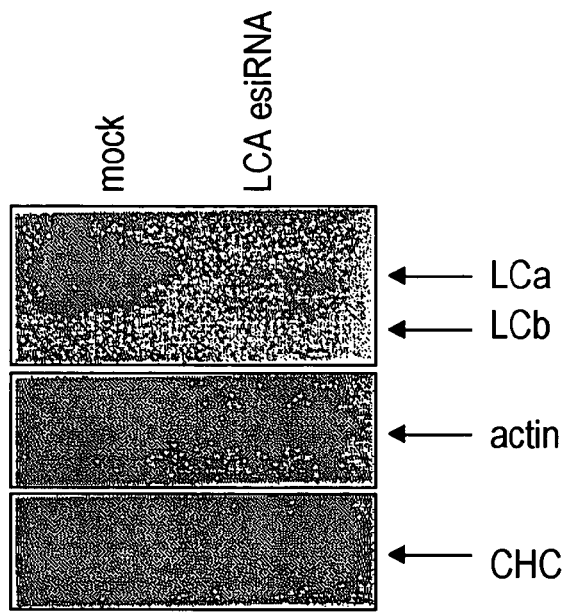
FIGS. 5A-C: Silencing of endogenous mammalian genes with esiRNA. (a) Specific inhibition of expression of clathrin LCa. Western blotting was used to analyse Hela cells that had been mock transfected or transfected with LCa esiRNA. Three antibodies were used: rabbit serum which recognizes both LCa and LCb, monoclonal antibody against actin and monoclonal TD.1 against the clathrin heavy chain (CHC). (b) Selective reduction of c-Myc expression. 293 cells were transfected with buffer, c-myc esiRNA, or R-luc esiRNA. Western blotting was performed with antibodies against c-myc and actin 72 hours after transfection. (c) Dose-dependent inhibition of Cdk2 expression by esiRNA. 293 cells were transfected with indicated doses of Cdk2 esiRNA, western blotting was performed with antibodies against Cdk2 and Cyclin A 5 days after transfection.

To test whether the expression of endogenous genes could be silenced we targeted a wide variety of genes, including those with either abundant long-lived or rare short-lived transcripts/proteins. We first attempted to silence the expression of the clathrin light chain a (LCa) in Hela cells. We examined the level of LCa protein 5 days after esiRNA transfection to allow turnover of the protein, whose half-life is 24 hours (21). Western blot analysis revealed that the LCa chain was reduced up to 90% (FIG. 5a). Clathrin light chain b (LCb) was unaffected although it has 66% homology in DNA sequence with LCa and was recognized by the same antibody. A cross-silencing between LCa and LCb was not expected because these two genes do not share any uninterrupted DNA sequence longer than 21 nt in length. LCa turns over independently of the other subunits of clathrin. Accordingly, inhibition of LCa expression did not affect the expression of clathrin heavy chain (FIG. 5a). We found that esiRNA-treated cells grew normally despite dramatically reduced LCa protein. This is presumably due to functional redundancy between LCa and LCb. For example, complete loss of LCa in PC12 cells has been reported to have little effect on clathrin-mediated endocytosis and secretion (21).

Figure 5B:
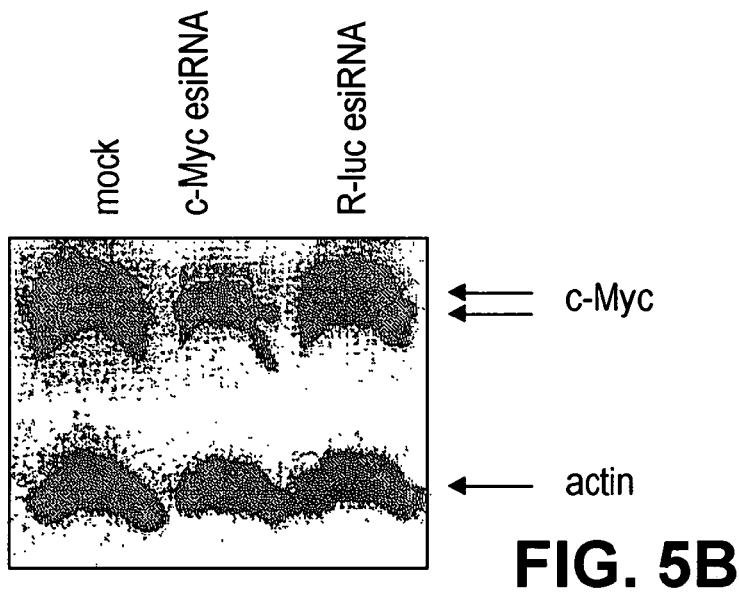
Figure 5C:
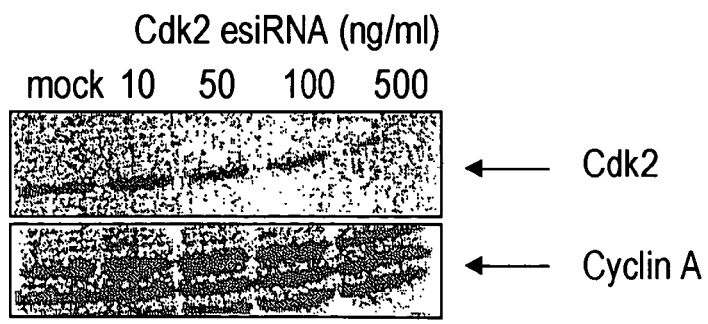

We next asked whether esiRNA could be used to inhibit genes whose mRNA and protein products are low in abundance and relatively unstable. As an example, we transfected c-myc esiRNA into 293 cells. We observed that the level of c-myc protein was reduced by about 70% (FIG. 5b). Inhibition was sequence-specific because actin expression was not affected and unrelated R-luc esiRNA failed to reduce c-myc expression. In addition, we observed specific reduction of cyclin-dependent kinase, Cdk1 and Cdk2, in response to treatment with their corresponding esiRNA (FIG. 5c). The RNase III/esiRNA protocol was also used to specifically reduce expression of chaperon p23). To date, we have successfully used esiRNA to inhibit the expression of 7 diverse genes in cell culture. These examples established esiRNA as a valuable tool for selective depletion of gene products in mammalian cells.

Our results demonstrate that the short RNAs produced by hydrolysis with E. coli RNase III can specifically silence gene expression in cultured mammalian cells, in a manner similar to that observed with synthetic siRNA. There are several advantages to the esiRNA protocol presented here. Because esiRNA can potentially target multiple sites within an mRNA, the requirement of screening efficient siRNA for individual genes is eliminated. Targeting of multiple sites would also be important in efforts to reduce viral replication because it can restrict the emergence of siRNA-resistant strains produced by base pair mismatches. The protocol is technically simple and quick, and it is effective on a wide range of proteins in different mammalian cell lines. Large-scale functional genomic studies with dsRNA have already been successful in C. elegans, but comparable analysis is still lacking in vertebrates (22-23). Because of its attributes, RNAi with esiRNA could be easily adapted for analysis of gene functions at the genome scale in cultured mammalian cells. A reverse genetics approach with esiRNA could be particularly useful to identify genes essential for viability because it is difficult to make stable mutants for those genes. Cancer cells are genetically different from their normal cell counterparts, often having undergone at least a half-dozen mutations (24). EsiRNA could be used to search genes whose downregulation specifically kills tumor cells with primary defect, a synthetic lethal approach that simultaneously identifies and validates appropriate new drug targets.

II. Materials and Methods

A. Protein Expression and Purification

The E. coli RNase III coding sequence was amplified with PCR from the bacterial strain DH5α genomic DNA with the upstream primer cgc gga tcc aac ccc atc gta att aat cgg ctt ca (SEQ ID NO:1) and downstream primer gac gtc cga tcg caa t (SEQ ID NO:2), and cloned into Bam HI and Sma I of pGEX-2T (Pharmacia). To produce GST-RNase III protein, the bacterial strain BL21(DE3) carrying the expression vector was grown at 37° C. to an $OD_{600}$ of 0.5 and induced with 1 mM IPTG for 2 hours. GST-RNase III was purified with glutathione-agarose beads according to the manufacture's instruction (Pharmacia), dialyzed against 20 mM TrisHCL, 0.5 mM EDTA, 5 mM MgCL2, 1 mM DTT, 140 mM NaCL, 2.7 mM KCL, 30% glycerol, pH 7.9 over night, and kept at −20° C. Approximately 1 mg of RNase III was purified from 1 liter of culture. There was no significant loss of enzyme activity after 6 month of storage.

B. Single-Strand RNA Synthesis and Preparation of dsRNA

The siRNAs CS1 and CS2 were synthesized chemically (Dharmacon). SiRNAs, T1 to T6, and short RNA hairpins, H1 to H6, were synthesized using the MEGAshortscript™ kit (Ambion) from oligo DNA templates carrying a phage T7 promoter at one end. All siRNAs were 21 nucleotide long and had 2-nucleotide 3' overhangs. All short hairpin RNAs had a 24 bp stem with a UCU loop and an extra GGGA at 5' end for efficient transcription in vitro. Other RNA strands were individually synthesized using the MEGAscript™ kit (Ambion) from PCR-derived linear templates carrying a phage T7 promoter at both ends. dsRNA was formed by annealing as described previously (16).

The ends of the dsR-457 RNAs corresponded to 1200-1656 in pRL-CMV (Promega). The F-luc RNAs corresponded to the following position in pEGFPLuc (Clontech): dsF-592, 1455-2046; CS1, 1520-1538; CS2, 1900-1918; T1, 603-621; T2, 624-642; T3, 2448-2466; T4, 2994-3012; T5, 3013-3031; T6, 3049-3067; H1, 989-1012; H2, 1520-1543; H3, 2529-2552; H4, 2601-2624; H5, 2906-2929; H6, 2947-2970. Templates for LCa and Cdk1 dsRNA represented the full coding sequences of their genes. Templates for the 681 bp c-myc dsRNA were amplified with forward primer gactcaacgttagct-tcaccaaca (SEQ ID NO:3) and reverse primer ggactccgtcgag-gagagcaga (SEQ ID NO:4). All these primers had appended 18 base phage promoters.

C. Production and Purification of Short RNA Duplexes

To prepare esiRNAs for F-luc and R-luc, 100 μg of dsRNAs were digested by 1 μg of recombinant RNase III in a 200 μl reaction buffer (same as dialysis buffer except 5% glycerol) for 15 min at 37° C. Reactions were terminated by adding EDTA to 20 mM and the products separated on 12% polyacrylamide gel, 1×TBE. A 10 bp DNA marker was used to estimate the migration of RNA duplexes. Short RNAs of appropriate sizes were eluted from gel slices by soaking in 1 M $(NH_4)_2AC$ at 37° C. over night and recovered by ethanol precipitation. The precipitate was dissolved in TE buffer at 1.0 μg/μl. For other genes, 100 ug of dsRNAs were digested with 0.2 ug of RNase III for one hour at 21° C. and reactions were loaded onto QIAquick spin columns after being supplemented with 5 volume of PN buffer (QIAquick nucleotide removal kit, Qiagen). Flowthrough usually contained RNA from 15 to 25 base paires, which was precipitated by ethanol and dissolved in TE buffer. The concentration of esiRNA was determined by $UV_{260}$.

D. Cell Culture, Nucleic Acid Transfections and Luciferase Assays

C33A human cervical carcinoma cell line, HeLa human cervical epithelioid carcinoma cell line, and 293 transformed human embryonic kidney cells were obtained from American Type Culture Collection and grown in DMEM. The hTERT-RPE1 cell line (Clontech Laboratories, Inc) is a human retinal pigment epithelial (RPE) cell line that stably expresses the human telomerase reverse transcriptase subunit (hTERT). hTERT-RPE1 cells were permanently transfected with a F-luc expression construct to express firefly luciferase from chromatin templates and were grown in DEME/F12 medium. *Drosophila* S2 cells were grown in Schneider medium. All medium was from Life Technology and supplemented with 10% FBS (vol/vol). Mammalian cells were cultured at 37° C., S2 cells at room temperature.

To silence luc expression from plasmid templates, plasmid DNA and siRNAs were cotranfected using Superfect (Qiagen). Cells were transfected at 50-70% confluence in 24-well plates for 2.5 hours and then changed to fresh medium. Unless otherwise described, transfections utilized one μg of DNA per well in 0.5 ml transfection medium (0.5 μg pEGFPLuc, 0.1 μg pRL-SV40, and 0.4 μg pUC19, and 47 nM esiRNA). Data were expressed as mean ratio of relative Luc activities (F-luc/R-luc or R-luc/F-luc) and normalized to that in cells transfected with DNA only. Error bars equal +/− one standard deviation. To silence F-luc expression from chromatin templates in RPE cells, 0.2 μg esiRNA was transfected into each well of a 6-well plate using lipofectamine 2000 for 3 hours and then changed to the fresh medium. Luciferase activity was measured as described previously (16). Protein concentrations were measured by Bradford assays (Biorad).

To silence endogenous gene expression, cells were cotransfected with 1 μg esiRNA using lipofectamine 2000.

E. In Vitro RNAi Assay

Preparation of cell extracts and in vitro RNAi were carried out according to the previous description (20). The Hela cells ($2 \times 10^7$) were washed in PBS and resuspended in a hypotonic buffer (10 mM HEPES pH 7.0, 2 mM $MgCl_2$ and 6 mM mercaptoethanol) and lysed. Cell lysates were centrifuged at 20,000 g for 30 min. We stored supernatants at −80 C. As described previously (16), mRNAs were produced using MAXIscript™ kit (Ambion) and were uniformly labelled during the transcription reaction with $^{32}P$-labelled UTP. For in vitro RNAi, 10 μl of extracts were incubated for indicated times at 37 C with 100 nM esiRNA in a 20 μl of reaction containing 20 mM Hepes pH 7.0, 1 mM MgOAC, 100 mM $K_2$ (OAC), 5 mM DTT, 500 uM NTP and 2 units of RNasin (Promega).

F. Western Blotting

For analysis of clathrin light chain and heavy chain, cells extracts were prepared as described previously (21, 25). For c-myc, Cdk1 and Cdk2, transfected cells grown in 6-well plates were harvested in PBS buffer containing 1% NP-40 and mixed with an equal volume of SDS sample buffer. Equal amounts of total protein were separated on 12.5% polyacrylamide gels and transferred to nitrocellulose. Standard immunostaining was carried out using ECL (Amersham Pharmacia). Rabbit serum which recognizes both LCa and LCb, and monoclonal TD.1 against clathrin heavy chain were described previously (21, 25). Anti-c-Myc antibody, N262, and antibodies for Cyclin A and Cdk2 are from Santa Cruz biotechnology, anti-actin antibody from Sigma.

REFERENCES

1. Sharp, P. A. (2001) Genes Dev. 15, 485-490.
2. Bosher, J. M. & Labouesse, M. (2000) Nat. Cell Biol. 2, E31-36.
3. Bernstein, E., Caudy, A. A., Hammond, S. M. & Hannon, G. J. (2001) Nature 409, 363-366.
4. Elbashir, S. M., Lendeckel, W. and Tuschl, T. (2001) Genes Dev. 15, 188-200.
5. Nishikura, K. (2001) Cell 16, 415-418.
6. Paddison, P. J., Caudy, A. A. & Hannon, G. J. (2002) Proc. Natl. Acad. Sci. USA 99, 1443-1448.
7. Yang, S., Tutton, S., Pierce, E. & Yoon, K. (2001%) Mol. Cell Biol. 21, 7807-7816.
8. Wianny, F. & Zernicka-Goetz, M. (2000) Nat. Cell Biol. 2, 70-75.
9. Stark, G. R., Kerr, I. M., Williams, B. R., Silverman, R. H. & Schreiber, R. D. (1998) Annu. Rev. Biochem. 67, 227-264.
10. Elbashir, S. M., Harborth, J., Lendeckel, W., Yalcin, A., Weber, K. & Tuschl, T. (2001) Nature 411, 494-498.
11. Caplen, N. J., Parrish, S., Imani, F., Fire, A. & Morgan, R. A. (2001) Proc. Natl. Acad. Sci. USA 98, 9742-9747.
12. Paddison, P. J., Caudy, A. A., Bernstein, E., Hannon, G. J. & Conklin, D. S. (2002) Genes Dev. 16, 948-958.
13. Brummelkamp, T. R., Bernards, R. & Agami, R. (2002) Science 296, 550-553.
14. Holen, T., Amarzguioui, M., Wiiger, M. T., Babaic, E. & Prydz, H. (2002) Nucleic Acids Res. 30, 1757-1766.
15. Harborth, J., Elbashir, S. M., Bechert, K., Tuschl, T. & Weber, K. (2001) J. Cell Sci. 114, 4557-4565.
16. Yang, D., Lu, H. and Erickson, J. W. (2000) Curr. Biol. 10, 1191-1200.

17. Amarasinghe, A. K., Calin-Jageman, I., Harmouch, A., Sun, W. & Nicholson, A. W. (2001) Methods Enzymol. 342, 143-158.

18. Elbashir, S. M., Martinez, J., Patkaniowska, A., Lendeckel, W. & Tuschl, T. (2001) EMBO J. 20, 6877-6888.

19. Zhang, K. and Nicholson, A. W. (1997) Proc. Natl. Acad. Sci. USA 94, 13437-13441.

20. Zamore, P. D., Tuschl, T., Sharp, P. A. & Bartel, D. P. (2000) Cell 101, 25-33.

21. Action, S. L., Wong, D. H., Parham, P., Brodsky, F. M. & Jackson, A. P. (1993) Mol. Biol. Cell 4, 647-660.

22. Gonczy, P. et al. (2000) Nature 408, 331-336.

23. Fraser, A. G., Karnath, R. S., Zipperlen, P., Martinez-Campos, M., Sohrmann, M. & Ahringer, J. (2000) Nature 408, 325-330.

24. Hanahan, D. & Weinberg, R. A.(2000) Cell 100, 57-70.

25 Nathke, I. S., Heuser, J., Lupas, A., Stock, J., Turck, C. W. & Brodsky, F. M.(1992) Cell 68, 899-910.

We claim:

1. A method of inhibiting expression of a mammalian gene, the method comprising the steps of:
   (i) providing double stranded RNA having a sequence at least 95% identical to a sequence of mRNA transcribed from the mammalian gene over a comparison window of 200 continuous residues;
   (ii) digesting the double stranded RNA with *E. coli* RNAse III in vitro to form a plurality of siRNAs capable of interacting with multiple sites of the mRNA, wherein the siRNAs are 20-25 nucleotides in length; and
   (iii) transfecting mammalian cells with the plurality of siRNAs, thereby specifically inhibiting expression of the mammalian gene by at least 50%.

2. The method of claim 1, wherein the siRNAs are 21-23 nucleotides in length.

3. The method of claim 1, wherein the double stranded RNA is synthetic.

4. The method of claim 1, wherein the double stranded RNA comprises single stranded RNA isolated from a naturally occurring RNA population.

5. The method of claim 1, wherein the double stranded RNA comprises single stranded RNA corresponding to a naturally occurring RNA population.

6. The method of claim 1, wherein the double stranded RNA is provided by synthesizing an RNA and its complement, and hybridizing the RNA and its complement to form double stranded RNA.

7. The method of claim 1, wherein the siRNA is from mammalian RNA.

8. The method of claim 1, wherein the siRNAs are synthetic and have sequences identical to the mammalian gene.

9. The method of claim 1, wherein the at least 95% is 100%.

10. The method of claim 1, wherein with *E. coli* RNAse III is a GST- *E. coli* RNAse III fusion protein.

11. The method of claim 1, wherein the expression of the mammalian gene is inhibited by at least 90%.

* * * * *

UNITED STATES PATENT AND TRADEMARK OFFICE
CERTIFICATE OF CORRECTION

| | | |
|---|---|---|
| PATENT NO. | : 8,119,610 B2 | Page 1 of 1 |
| APPLICATION NO. | : 10/448612 | |
| DATED | : February 21, 2012 | |
| INVENTOR(S) | : Yang et al. | |

It is certified that error appears in the above-identified patent and that said Letters Patent is hereby corrected as shown below:

On the Title page:

In Item (56), the References Cited section, page 1, first column, line 39,
under the OTHER PUBLICATIONS subsection: please delete "Check Nature" and insert
--Check, E., Nature--.

In Item (56), the References Cited section, page 1, second column, line 48,
under the OTHER PUBLICATIONS subsection: please start the "Zamore, Phillip D. et al." reference on a new line.

In the Specification:

In the STATEMENT AS TO RIGHTS TO INVENTIONS MADE UNDER FEDERALLY SPONSORED RESEARCH AND DEVELOPMENT subsection, Column 1, Line 16, please delete "This invention was made with government support under NIH grant CA44338. The Government has certain rights in this invention." and insert --This invention was made with government support under grant no. CA44338 awarded by the National Institutes of Health. The government has certain rights in the invention.--

Signed and Sealed this
Twenty-sixth Day of June, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:upstream
      primer

<400> SEQUENCE: 1
cgcggatcca acccatcgt aattaatcgg cttca                             35

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:downstream
      primer

<400> SEQUENCE: 2
gacgtccgac gatggcaat                                              19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:forward
      primer

<400> SEQUENCE: 3
gactcaacgt tagcttcacc aaca                                        24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:reverse
      primer

<400> SEQUENCE: 4
ggactccgtc gaggagagca ga                                          22